United States Patent
Wong et al.

(10) Patent No.: US 11,607,309 B2
(45) Date of Patent: Mar. 21, 2023

(54) NEURAL PREDICTORS OF LANGUAGE-SKILL OUTCOMES IN COCHLEAR IMPLANTATION PATIENTS

(71) Applicants: THE CHINESE UNIVERSITY OF HONG KONG, Hong Kong (CN); ANN & ROBERT H. LURIE CHILDREN'S HOSPITAL OF CHICAGO, Chicago, IL (US)

(72) Inventors: Patrick Chun Man Wong, Hong Kong (CN); Gangyi Feng, Hong Kong (CN); Nancy Melinda Young, Wilmette, IL (US)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 1060 days.

(21) Appl. No.: 16/224,564

(22) Filed: Dec. 18, 2018

(65) Prior Publication Data
US 2019/0192285 A1 Jun. 27, 2019

Related U.S. Application Data

(60) Provisional application No. 62/609,305, filed on Dec. 21, 2017.

(51) Int. Cl.
*A61F 2/18* (2006.01)
*G16H 20/40* (2018.01)
(Continued)

(52) U.S. Cl.
CPC ............ *A61F 2/18* (2013.01); *A61B 5/0042* (2013.01); *A61B 5/055* (2013.01); *A61B 5/4851* (2013.01);
(Continued)

(58) Field of Classification Search
CPC ..... A61F 2/18; A61F 2002/183; G16H 20/40; G16H 30/20; G16H 50/70; G16H 50/20;
(Continued)

(56) References Cited

U.S. PATENT DOCUMENTS 7,899,922 B2  3/2011 Collins et al.
2007/0225776 A1*  9/2007 Fritsch ............... A61N 1/0541
607/57
(Continued)

FOREIGN PATENT DOCUMENTS

WO   2015/064665 A1   5/2015

OTHER PUBLICATIONS

Deng et al., "White Matter Anisotropy in the Left Anterior Superior Temporal Region Predicts Speech Perception Improvement in Young Cochlear Implant Recipients," CI 2017 Pediatric 15th Symposium on Cochelar Implants in Children, Jul. 26-29, 2017, San Francisco, CA, USA, 2 pages.
(Continued)

*Primary Examiner* — Michael Tomaszewski
*Assistant Examiner* — Rachael Sojin Stone
(74) *Attorney, Agent, or Firm* — Kilpatrick Townsend & Stockton LLP (57) ABSTRACT

Machine-learning techniques are used to train a classifier to predict auditory and language skills improvement in a patient who is a candidate for cochlear implantation (CI). One or more images of portions of the patient's brain are obtained, and quantitative data is extracted that represents the composition of one or more brain areas related to auditory and/or cognitive processing. For training of the classifier, data is obtained for previous CI patients whose improvement in language skills has been measured. Once
(Continued)

trained, the classifier can be used to predict a likely degree of improvement in a prospective CI patient's auditory and language skills.

20 Claims, 11 Drawing Sheets
(2 of 11 Drawing Sheet(s) Filed in Color)

(51) Int. Cl.
| | | |
|---|---|---|
| *G16H 30/20* | (2018.01) | |
| *G16H 50/20* | (2018.01) | |
| *A61B 5/055* | (2006.01) | |
| *G16H 30/40* | (2018.01) | |
| *G16H 50/70* | (2018.01) | |
| *A61B 5/00* | (2006.01) | |

(52) U.S. Cl.
CPC .......... *A61B 5/7275* (2013.01); *G16H 20/40* (2018.01); *G16H 30/20* (2018.01); *G16H 30/40* (2018.01); *G16H 50/20* (2018.01); *G16H 50/70* (2018.01); *A61B 2576/026* (2013.01); *A61F 2002/183* (2013.01)

(58) Field of Classification Search
CPC ...... G16H 30/40; A61B 5/0042; A61B 5/055; A61B 5/4851; A61B 5/7275; A61B 2576/026
USPC .......................................... 706/12; 705/2, 3
See application file for complete search history.

(56) References Cited

U.S. PATENT DOCUMENTS

| | | | |
|---|---|---|---|
| 2013/0253625 A1* | 9/2013 | Simon .................. | A61N 1/0546 607/116 |
| 2019/0247662 A1* | 8/2019 | Poltroak .............. | A61B 5/0816 |
| 2021/0041953 A1* | 2/2021 | Poltorak ................ | A61B 5/377 |

OTHER PUBLICATIONS

Feng, et al., "Morphological Neural Preservation Underlies Speech Perception Improvement in Young Cochlear Implant Recipients," CI 2017 Pediatric 15th Symposium on Cochelar Implants in Children, Jul. 26-29, 2017, San Francisco, CA, USA, 2 pages.

* cited by examiner

NEURAL PREDICTORS OF LANGUAGE-SKILL OUTCOMES IN COCHLEAR IMPLANTATION PATIENTS

CROSS-REFERENCE TO RELATED APPLICATIONS

This application claims priority to U.S. Provisional Application No. 62/609,305, filed Dec. 21, 2017, the disclosure of which is incorporated herein by reference.

BACKGROUND

The present disclosure relates generally to predicting communication outcomes in patients receiving cochlear implants and in particular to neural predictors of auditory and/or language skills outcomes in such patients.

It is estimated that, in the United States, about 2 to 3 children out of 1,000 are born deaf or hard of hearing. Cochlear implantation (CI), which involves the implantation of an electrode array into the cochlea, with the electrode array connected to a stimulator that is receptive to audio input, provides the promise of improving hearing for many of these children. However, it is also estimated that only about 50% of the pediatric candidate population has received CI. Reasons for such low adoption may include the cost, combined with the uncertainty of the outcome.

At present, various standard tests are used to determine whether a patient is a candidate for cochlear implantation (CI). In addition to assessments of hearing impairment, these tests generally include magnetic resonance imaging (MRI) (to determine if cochlear malformations or eighth nerve abnormalities are present and to obtain baseline anatomy of the brain as the presence of the CI creates artifacts that may limit post-CI brain imaging) as well as assessments of the effectiveness of amplification (since amplification by external hearing aids, when effective, avoids the risks associated with surgery and is associated with lower cost).

However, even among pediatric patients identified as candidates, including those with normal preoperative imaging and without additional diagnoses associated with developmental delay, CI has highly variable outcomes. Some children are able to attain age-appropriate auditory and/or language skills while others experience persistent delays. One comprehensive study of CI outcomes for children under 5 years of age (J K Niparko et al., "Spoken language development in children following cochlear implantation," *JAMA* 303(15):1498-1506 (2010)) found that, although CI children performed better than expected by their pre-implantation scores in expressive and receptive language, their performance was still significantly lower than that of their normal hearing (NH) peers. Further, tremendous variability in outcomes was observed, with some but not all CI children catching up to their peers within two years.

Better tools for predicting the outcome of CI for a particular patient would aid in treatment planning. For instance, the initial decision whether to perform CI could be informed by the degree of significant improvement in receptive and expressive auditory and/or language skills and the time frame over which improvement is likely to occur. In addition, information about predicted outcome for a particular patient may be helpful for post-surgical management, including developing a plan for post-surgical language therapy (e.g., listening and spoken language therapies, music therapy, as well as visual communication methods).

SUMMARY

Certain embodiments of the present invention relate to techniques for pre-surgical prediction of the outcome of cochlear implantation (CI) for an individual patient. One or more images of portions of the patient's brain are obtained, e.g., using magnetic resonance imaging (MRI) or other imaging techniques. From the one or more images, quantitative data is extracted that represents the composition of one or more brain areas related to auditory and/or cognitive processing. In some embodiments, the data includes data representing at least one brain area that is not typically affected by auditory deprivation. The quantitative data is analyzed using a machine-learning algorithm that has been trained using corresponding data from a set of previous patients whose pre-surgical and post-surgical levels of auditory (including word recognition) and language skills have been measured. Based on the analysis, a predicted outcome can be generated for the individual patient. The predicted outcome may include, for example, a predicted level of auditory and/or language skill (or predicted degree of improvement in auditory and/or language skills) that the patient is likely to attain. The improvement may be related to awareness and understanding of environmental sounds, word understanding, spoken language, and/or visual language. The predicted outcome can be provided to a clinician, for use in pre-operative counseling of patients (or their parents or guardians if the patient is a child) regarding the likely range of benefit and treatment planning (e.g., developing a post-surgical treatment plan that may include specific types and intensity (dose) of hearing and language-skills therapy or other interventions).

The following detailed description, together with the accompanying drawings, will provide a better understanding of the nature and advantages of the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Certain embodiments of the present invention relate to techniques for pre-surgical prediction of the outcome of cochlear implantation (CI) for an individual patient. One or more images of portions of the patient's brain are obtained, e.g., using magnetic resonance imaging (MRI) or other imaging techniques. From the one or more images, quantitative data is extracted that represents the composition of one or more brain areas related to auditory and/or cognitive processing. In some embodiments, the data includes data representing at least one brain area that is not typically affected by auditory deprivation. The quantitative data is analyzed using a machine-learning algorithm that has been trained using corresponding data from a set of previous patients whose pre-surgical and post-surgical levels of auditory (including word recognition) and/or language skills have been measured. Based on the analysis, a predicted outcome can be generated for the individual patient. The predicted outcome may include, for example, a predicted level of auditory and/or language skills (or predicted degree of improvement in auditory and/or language skills) that the patient is likely to attain. The improvement may be related to awareness and understanding of environmental sounds, word understanding, spoken language, and/or visual language. The predicted outcome can be provided to a clinician, for use in pre-operative counseling of patients (or their parents or guardians if the patient is a child) regarding the likely range of benefit and treatment planning (e.g., developing a post-surgical treatment plan that may include specific types and intensity (dose) of hearing and language-skills therapy or other interventions).

As used herein, "language" refers to systems of communications that rely on symbols, which can include spoken, auditory, visual, sign, written, and/or gestural modalities and can include expressive and/or receptive components. "Language skill" of a patient can be measured by various techniques to assess competence, representation, and/or processing levels based on responses directly obtained from the patient by a clinician and/or caregiver reports provided to the clinician.

Overview

Figure 1:
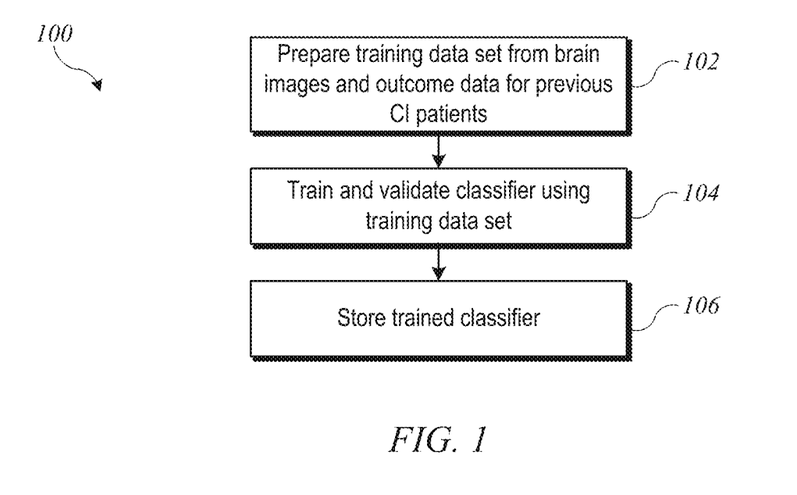
FIG. 1 shows a flow diagram of a process for training an automated (machine-learning) classifier to predict outcomes of cochlear implantation (CI) for individual patients according to an embodiment of the present invention.

FIG. 1 shows a flow diagram of a process 100 for training an automated classifier to predict outcomes of CI for individual patients according to an embodiment of the present invention. Process 100 can be implemented using a suitably programmed computer system.

At block 102, a training data set is prepared. The training data set can include information obtained from patients who previously received a cochlear implant. The information obtained can include information extracted from images of the patient's brain prior to CI, such as MRI images. (Suitable images are routinely obtained from patients as part of pre-CI evaluation.) Extracting useful information can involve processing of the images, e.g., to reduce noise and to resample the images into voxels of useful size (e.g., 1 mm×1 mm×1 mm). The resampled images can be segmented into different tissue types (e.g., gray matter (GM), white matter (WM), and cerebrospinal fluid) using appropriately constructed templates. Spatial normalization and smoothing can be applied. In some embodiments, a masking template may be applied to select specific brain areas of interest based on working assumptions about which brain areas are most likely to be predictive of the outcome of CI. As shown in examples below, it is currently believed that brain areas with the most predictive power in this context are areas that are related to auditory and/or cognitive processing but not (typically) affected by auditory deprivation; brain areas that are affected by auditory deprivation tend to have less predictive power. Alternatively, analysis may be performed using whole-brain image data.

The information included in the training data set can also include information indicating the improvement in auditory and/or language skills achieved after CI. Improvement can be measured using a test of auditory, speech perception (word recognition), and/or language processing that is administered to a CI candidate before surgery (to establish a baseline) and again at intervals after activation and use of the CI system (e.g., six months after activation of the cochlear implant). One of many examples of commonly used test to measure development of auditory and speech recognition is the Speech Recognition Index in Quiet (SRI-Q) assessment battery (described in Wang et al., "Tracking development of speech recognition: longitudinal data from hierarchical assessments in the Childhood Development after Cochlear Implantation Study," *Otol. Neurotol.* 29(2): 240-245 (2008)). The SRI-Q provides a hierarchy of measures of speech recognition ability, from parental or caregiver reports for children with the lowest abilities to direct measures of speech perception for children with better auditory abilities, all on the same scale. Tests used may include, e.g., any or all of the Infant/Toddler Meaningful Auditory Integration Scale/Meaningful Auditory Integration Scale (IT-MAIS/MAIS, which is based on caregiver reports), the Early Speech Perception Test (ESP), the Multisyllabic Lexical Neighborhood Test (MLNT), the Lexical Neighborhood Test (LNT), the Phonetically Balanced Word Lists-Kindergarten assessment (PBK), and/or the Children's Hearing in Noise Test (HINT-C). Other examples of tests used to evaluate these skills include the Little Ears Auditory Questionnaire, the Pediatric AZ Bio, AZ Bio Sentence Test, and the consonant-nucleus-consonant (CNC) word test. A variety of tests or suites of assessments may be used, some of which include testing in the presence of background noise; the assessment should include a receptive component and may also include an expressive component. For children who are not from English-speaking homes or are learning a language other than English, other language-skill tests may be used.

An assessment battery such as SRI-Q allows for a comparison of performance across a range of ages (e.g., infancy to 5 years or infancy to 3.5 years). In some embodiments, the difference between pre-CI and post-CI assessment scores is used to assign each patient to a binary "low improvement" or "high improvement" classification. In other embodiments, the difference between pre-CI and post-CI test scores is used to rank patients according to degree of improvement. Specific examples are provided below.

At block 104, an automated classification algorithm (also referred to as a "classifier") may be trained using the training data set. Suitable algorithms include machine-learned classification algorithms such as a Support Vector Machine (SVM) or ranking SVM (RankSVM).

SVM is a machine-learned classification technique that takes as input a feature vector in a space of arbitrary dimension and a binary classification and maps the feature vector to a point in a classification space such that a hyperplane in the classification space (referred to as a "margin") separates the points corresponding to the (binary) classification of the corresponding feature vector. In most SVM implementations, the margin may be a "soft margin," allowing the classification to be less than 100% accurate. In the present context, the feature vector can be the voxel data generated for a given patient, and the binary classification can be "low improvement" or "high improvement," based on the magnitude of the difference between the patient's pre-CI and post-CI assessment scores.

RankSVM is a machine-learned classification technique whose goal is to construct ordered models that can be used to sort unseen data according to their degree of relevance or importance. RankSVM can be used to form ranking models by minimizing a regularized margin-based pairwise loss. RankSVM uses SVM to compute a weight vector that maximizes the difference of data pairs in ranking. In principle, RankSVM requires investigating every data pair as potential candidates for support vectors, and the number of data pairs is quadratic to the size of the training set. In practice, this can result in low computational efficiency for large training sets and/or large feature vectors. Accordingly, optimizations may be employed to increase computational efficiency; specific examples are described below.

Figure 2:
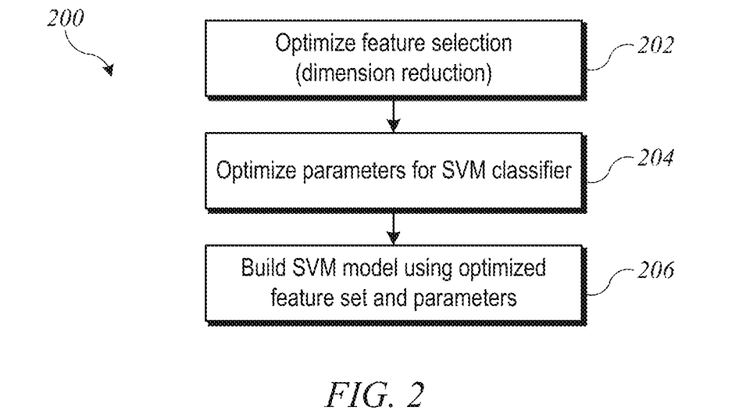
FIG. 2 shows an example of a training process that can be used to train an automated (machine-learning) classifier according to an embodiment of the present invention.

In some embodiments, training can be performed in phases (or levels). FIG. 2 shows an example of a training process 200 that can be used at block 104 of FIG. 1 according to an embodiment of the present invention. Process 200 implements a nested leave-one-out cross-validation (LOOCV) procedure with three levels of nesting for training an SVM or RankSVM according to an embodiment of the present invention.

At block 202, a first (inner) level of LOOCV is used to optimize feature selection. At this level, the goal is to reduce the set of features (or dimensions), e.g., removing non-relevant features, for improving model generalization. Various techniques can be used. Examples include principal component analysis (PCA) and the SVM-RFE (SVM Recursive Feature Elimination) procedure. PCA is a well-known technique to generate an orthogonal transform for a set of feature vectors that preserves the maximal amount of variance for a given number of (mutually orthogonal) components in the transform space. The SVM-RFE procedure is an iterative procedure that includes training an SVM classifier using the full feature set, computing a ranking weight for each feature, eliminating the feature with the lowest weight; this process is iterated to generate a an ordered list of features in order of their increasing contribution to the prediction of outcomes.

In either case, the feature-selection optimization can include cross-validating using k-fold LOOCV. Specifically, if there are N samples in the training data set (where each sample corresponds to a different patient), a "fold" can be performed using N-k samples for training and the remaining k sample(s) for testing; multiple folds corresponding to different selections of the k testing samples can be generated, and consistency of outcomes across folds is assessed to validate the selection.

At block 204, a second (middle) level of LOOCV is used to optimize parameters for the SVM. Linear and non-linear SVMs can be considered, and the SVM may have associated parameters that can be optimized at block 204 to optimize between accuracy and stability. For example, in typical SVM implementations, a parameter C characterizes a "soft margin" cost function that defines a tradeoff between error rate and stability, and parameter γ characterizes a Gaussian (radical basis function, or RBF) kernel. At this stage, SVMs can be trained using a number of possible combinations of parameters; LOOCV can be used to validate the selection of the optimal combination.

At block 206, using the optimal feature set from block 202 and the optimal parameter set from block 204, an SVM model can be built. A third (outer) level of LOOCV can be used at this stage to train SVM models based on N-k training samples and apply the trained model to classify the remaining k sample(s). In some embodiments, k can be, for example, 10% of the original training data set.

Referring again to FIG. 1, once the classifier has been trained and validated, the trained classifier can be stored (block 106) for future use with patients who are candidates for CI.

Figure 3:
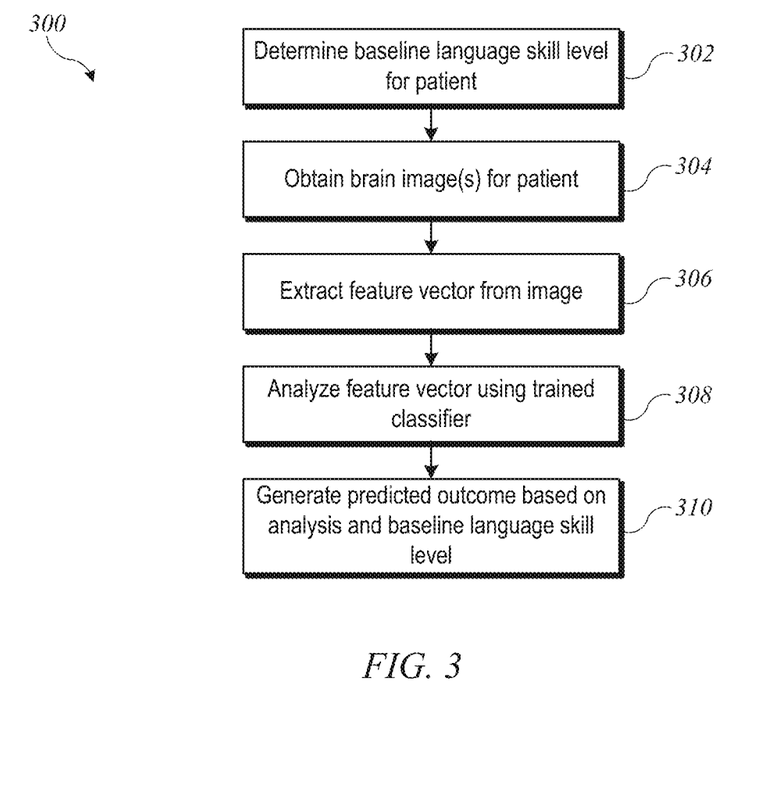
FIG. 3 shows a flow diagram of a process for predicting an outcome of CI for a new patient according to an embodiment of the present invention.

Use of the trained classifier is shown in FIG. 3, which is a flow diagram of a process 300 for predicting an outcome of CI for a patient according to an embodiment of the present invention. At block 302, a baseline auditory and/or language skill level for the patient is determined, e.g., by administering the same assessment that was used for the patients included in the training data. At block 304, brain images of the patient are obtained. The same technology used to obtain the images used in the training data set (e.g., MRI) is used. At block 306, a feature vector is extracted from the images. The techniques used should correspond to the techniques used to generate the feature vectors for the training data set, including resampling, segmentation by tissue type, normalization, masking, smoothing, etc. At block 308, the feature vector is analyzed using the trained classifier. For instance, the feature vector extracted at block 306 can be provided as input to an evaluation function of the trained classifier; the classifier applies the trained algorithm and outputs a classification result e.g., a predicted degree of improvement. Depending on the particular classifier, the predicted degree of improvement may correspond to a binary "low improvement" or "high improvement" classification or to a quantified degree of improvement. At block 310, the predicted degree of improvement and the patient's baseline auditory and/or language skill level can be used to generate a predicted outcome. This predicted outcome can be provided to a clinician for use in treatment planning.

Those skilled in the art will appreciate that a process similar to process 300 can also be used for validation of models during training process 100. A training sample can be input into a model that is being validated to obtain a "predicted" outcome. In this case, the actual outcome is also known, and comparing the "predicted" outcome to the actual outcome provides an indication of accuracy of the model.

In some embodiments, the model can be self-updating. For instance, once constructed, the model can be used to evaluate new (previously unseen) patients who are CI candidates. As patients who are evaluated using the model receive CI and have their outcomes determined, data for these patients can be added to the data set used for training, and the model can be updated from time to time (e.g., by repeating processes 100 and 200 using the enlarged data set). The updated model can then be used to predict outcomes for additional CI candidates.

Figure 4:
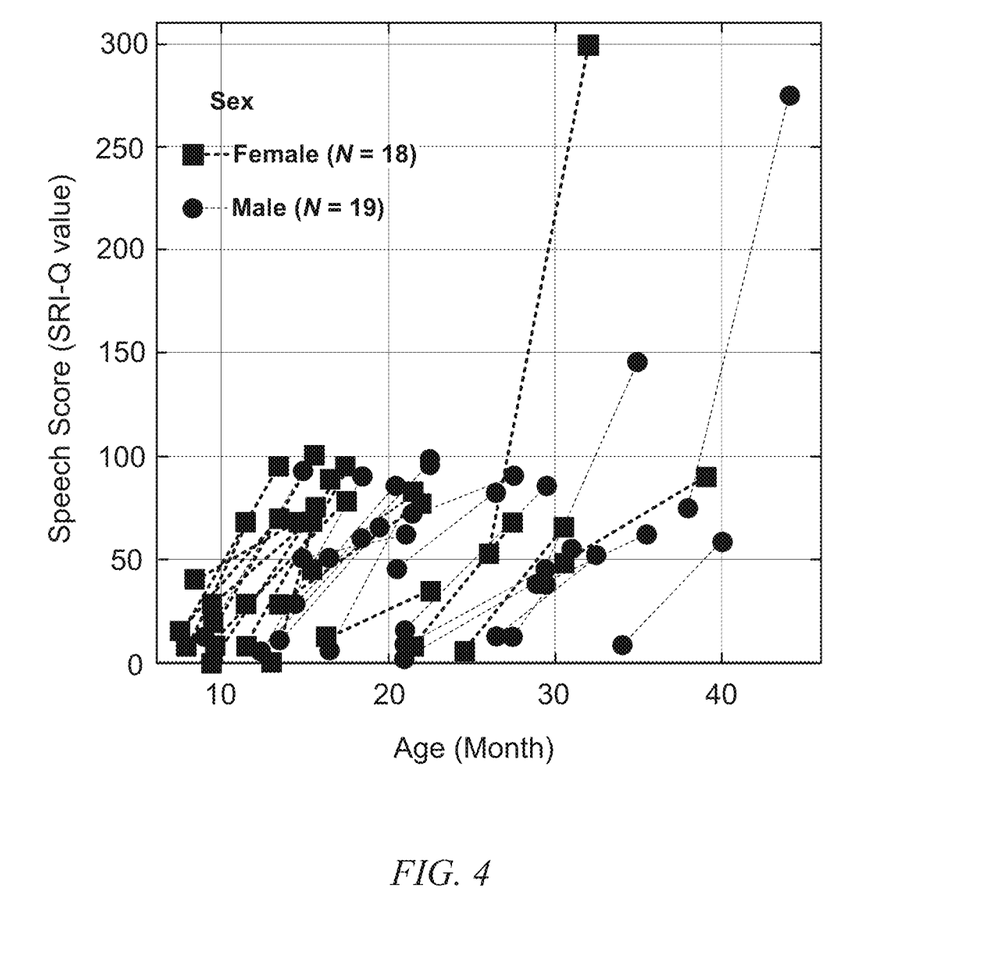
FIG. 4 shows examples of longitudinal changes in SRI-Q (speech-perception) scores for individual children in a group of children who received CI.

To further illustrate these processes, specific examples of classification models that have been trained to predict outcomes of CI in an experimental context will now be described. These examples are based on data obtained from 37 children who received CI before the age of 3.5 years. All of the children had bilateral sensorineural hearing loss rated as either severe to profound or moderate to severe, and were free of conditions known to adversely affect CI outcomes (e.g., gross brain malformation, severely malformed cochlea, cochlear nerve deficiency, post-meningitis deafness, or previous electrode array insertions). All had received hearing aids in the months prior to undergoing the MRI scans used in the examples described below. T1-weighted neuroanatomical MRI scans were performed prior to implantation using conventional techniques while the patients were under anesthesia to optimize comfort and minimize movement artifacts; these scans provided the image data used in examples below. Each child was evaluated using the SRI-Q assessment battery described above, before implantation and again at six months after activation of the implant. FIG. 4 shows longitudinal changes in SRI-Q scores for individual children in the CI group before and after implantation.

Selection of Brain Areas

As noted above, embodiments of the present invention can use "full brain" image data, with no attempt to select data representing particular brain areas or particular neuroanatomical or neurophysiological features. However, not all brain areas or features are equally significant for predicting outcomes of CI, and to improve computational efficiency, it may be desirable to use masking techniques to select brain areas or features that are most significant. Accordingly, in some embodiments of the present invention, masking is applied to select brain areas of interest. Various masking techniques may be used, with the same mask being applied for both training and testing.

Figure 5:
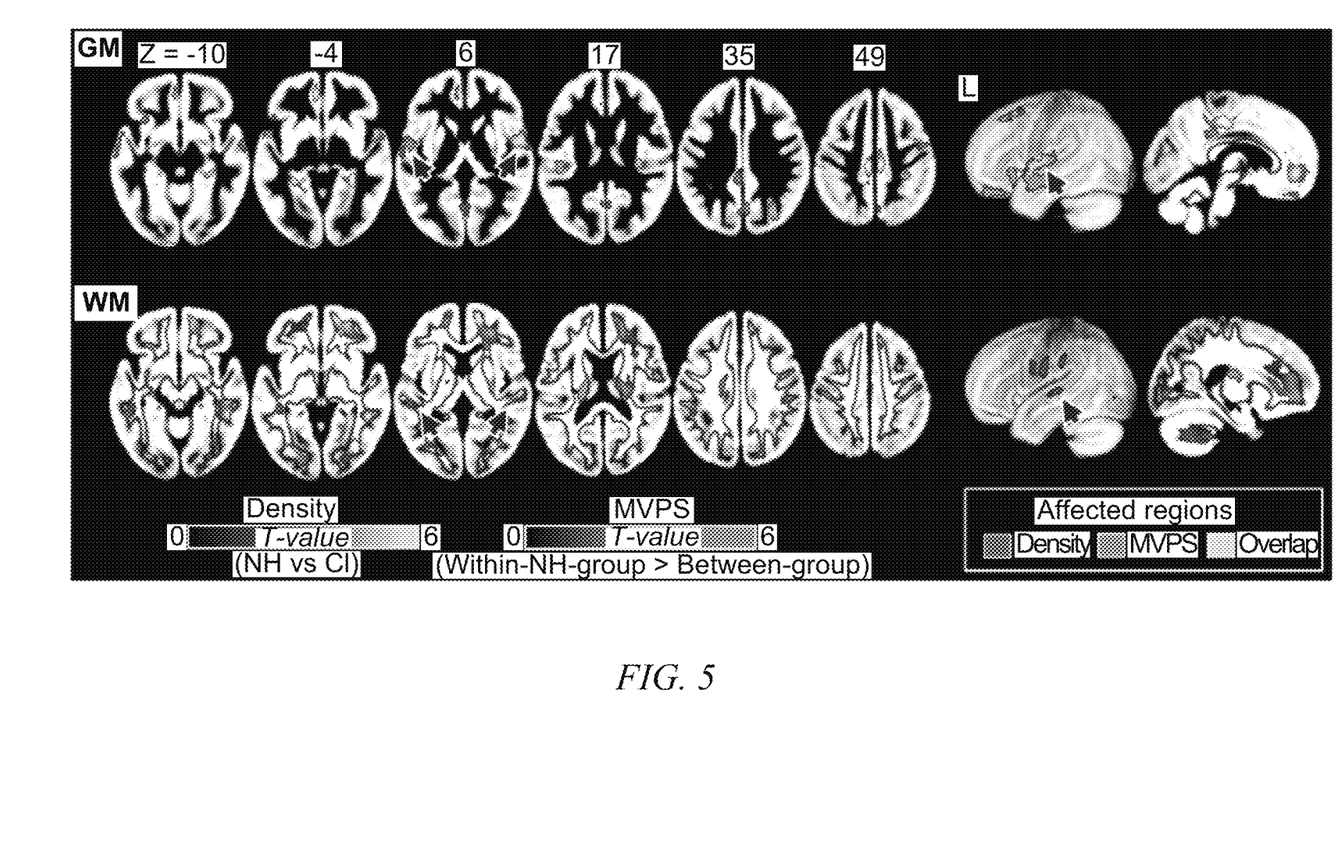
FIG. 5 shows group-comparison brain maps highlighting differences between a group of children who received CI and a group of age-matched children with normal hearing.

To assess potential masks, studies were conducted to identify morphological brain patterns that were potentially affected or unaffected by deafness. In addition to the CI group described above, MRI scans as described above were obtained for 40 children in the same age range with normal hearing (NH). Neuro-morphological analyses were performed to evaluate neural reorganization resulting from early deafness. One analysis used voxel-based morphometry (VBM), and the other used multi-voxel pattern similarity (MVPS). VBM reveals local tissue density (for gray and white matter), while MVPS measures similarity in local spatial morphological patterns that is independent of voxel-wise density; thus, the two types of analysis are relatively complementary. FIG. 5 shows group-comparison brain maps highlighting differences between children in the CI group and children in the NH group in VBM density (red/yellow scale) and MVPS patterns (green scale) for gray matter (GM, top row) and white matter (WM, bottom row). The maps were obtained by using two-sample t-tests with the variance of demographic variables controlled.

As shown in FIG. 5, children in the CI group showed significant differences in GM density as compared to children in the NH group across auditory temporal, medial frontal and posterior cingulate regions. Also, the between-group MVPS was significantly lower relative to within-NH-group MVPS across frontotemporal regions, suggesting that there was significant brain reorganization in morphological pattern for children in the CI group compared with age-matched children in the NH group. Blue arrows in FIG. 5 indicate the affected auditory regions, many of which were in the middle portion of the superior temporal region (e.g., the superior gyrus/superior temporal sulcus (STG/STS), including core and belt regions). White matter density for children in the CI group showed a significant decrease relative to children in the NH group. The between-group MVPS was also significantly lower relative to within-NH-group MVPS for frontal and temporal WM areas, suggesting there was a significant neuroanatomical reorganization in morphological pattern for children in the CI group compared with age-matched children in the NH group. The most apparent neuro-morphological differences between the groups were identified in the bilateral auditory cortex, especially the middle portion of STG. Less consistently across tissue and analysis type, neuro-morphological differences were also observed in the inferior frontal gyms, cingulate gyms, the occipital lobe, hippocampus, and the precuneus, suggesting that auditory deprivation may have begun to affect cross-modal and general cognitive brain regions, but these effects are less consistent than the effects found in the auditory cortex.

Based on the neuro-morphological analysis, brain templates were constructed to select "affected" regions (i.e., brain areas affected by auditory deprivation, which show significant differences between the CI and NH groups), "unaffected" regions (i.e., brain areas not affected by auditory deprivation, which do not show significant differences between the CI and NH groups), or "whole-brain" (including both the affected and unaffected areas) for use in the machine-learning algorithm. As described below, the unaffected regions provided higher classification accuracy.

Example 1: SVM Model

Figure 6A:
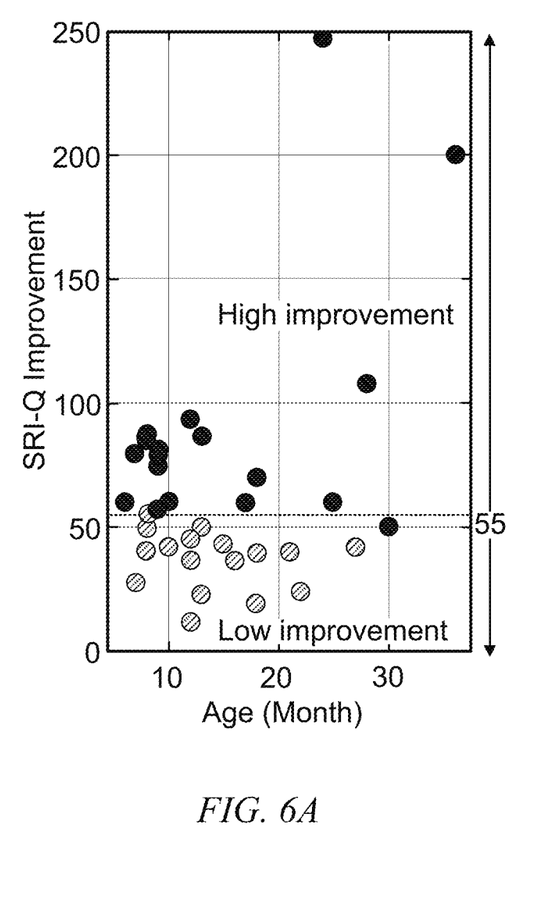
FIG. 6A shows SRI-Q improvement scores as a function of age and a division into high and low improvement classifications that can be used in some embodiments of the present invention.

SVM models were trained using the procedure described above on data for the CI group children. Three different brain templates, corresponding to affected regions, unaffected regions, and the whole brain, were used in separate instances of the training procedure. In each instance, neural data from each child in the CI group, masked by the appropriate brain template (or no masking in the case of whole-brain analysis), were converted to an S-by-V matrix where S is the number of children and V is the number of voxels. The matrix was normalized to a mean (M) of 0 and standard deviation (SD) of 1. Based on the difference between pre-implantation and post-activation SRI-Q scores, each child was assigned to either a "high" or "low" speech improvement classification. FIG. 6A shows SRI-Q improvement scores as a function of age for children in the CI group and a division into high and low speech improvement classifications based on a cutoff SRI-Q improvement score of 55. (Other cutoffs may be used.)

For each instance of the training procedure, the nested LOOCV procedure described above was applied. In each level, k-fold LOOCV was used with 90% of the data used for training and 10% of the data reserved for testing. To remove any confounding effect of differences in the number of voxels in different brain templates, for each instance, the same number of voxels were selected at the inner level of LOOCV (5,000 voxels, which is ~5% of a total number of voxels) across different brain templates. At the middle level of LOOCV, linear and nonlinear SVM classifiers using different parameter selections (C and γ) were compared. For the linear classifier, C=1 and γ=1/number of features. For nonlinear classifiers, 100 models were generated with a wide range of parameters. A nonlinear SVM classifier with radical base function (RBF) kernel that provided highest generalization accuracy based on the training set was chosen for the outer level of LOOCV. The training procedure was repeated 10,000 times (selecting a different subset of the data for testing in each case) in order to accurately estimate the distribution of classification accuracy. In addition, a null (or chance) distribution was generated by 10,000 instances of randomly assigning each child to one of the two classifications and repeating the training procedure.

Figure 6B:
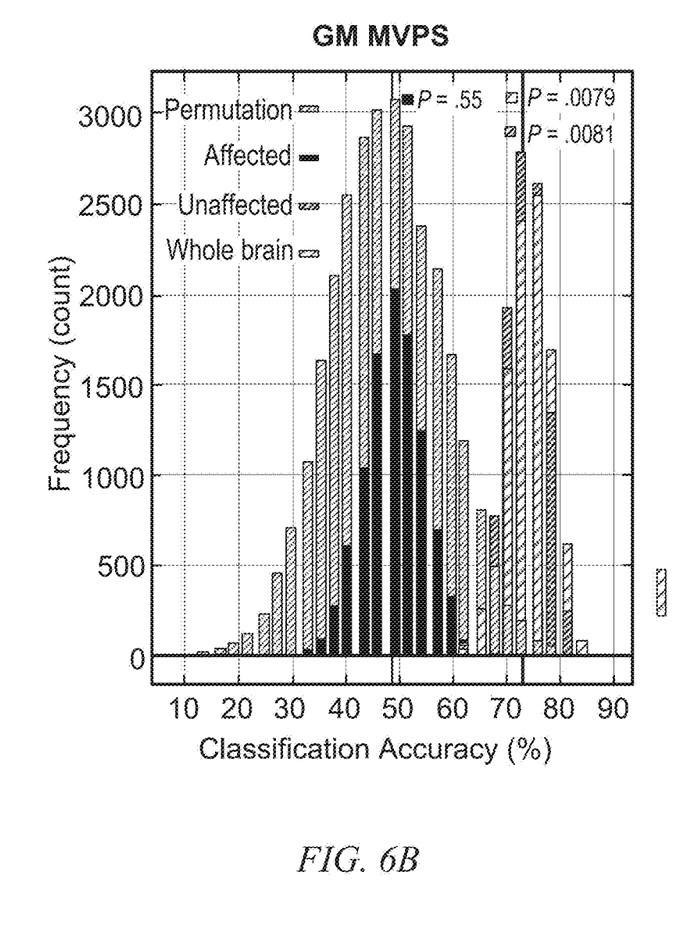
FIGS. 6B and 6C show classification-accuracy results obtained using gray-matter multi-voxel pattern similarity (MVPS) measures and white-matter MVPS measures, respectively, for trained support vector machine (SVM) classifiers according to various embodiments of the present invention.
Figure 6C:
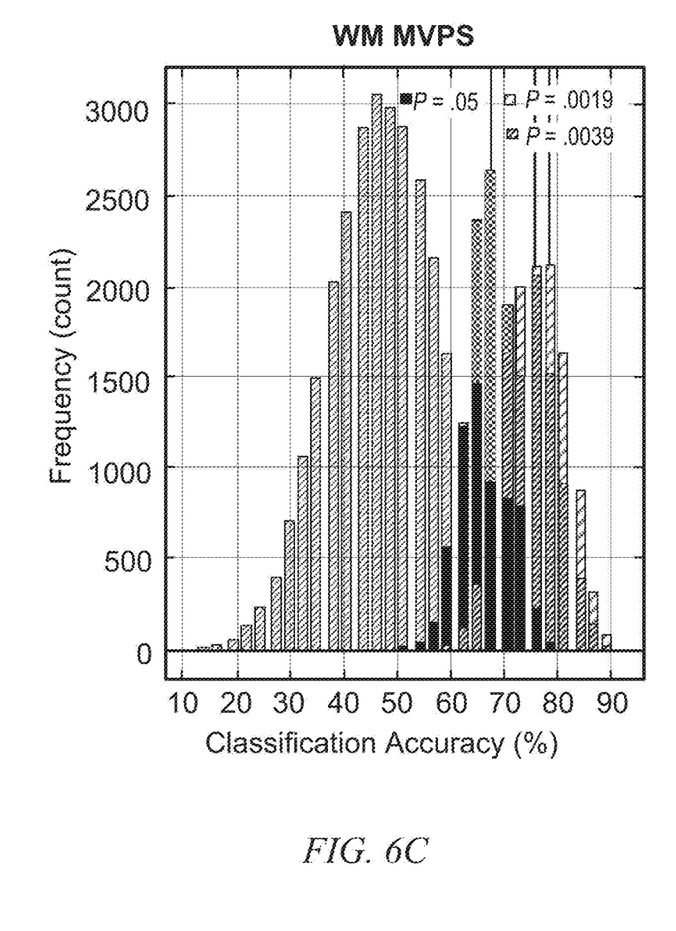

The training was performed separately for models using GM and WM tissue types and for both MVPS and density (VBM) measures as described above. FIG. 6B shows classification-accuracy results obtained using GM MVPS measures, and FIG. 6C shows classification-accuracy results obtained using WM MVPS measures. Each graph is a histogram showing the distribution of classification accuracy measured for different instances of the training procedure. Red bars correspond to training using a brain template that selected areas affected by auditory deprivation; green bars to a brain template that selected areas unaffected by auditory deprivation; blue bars to a whole-brain template. Gray bars show the null distribution. As can be seen, the models performed significantly better than chance, except for models using the affected template in the GM MVPS measure.

Example 2: RankSVM Model

To illustrate more quantitative prediction of speech improvement of individual CI children, linear RankSVM models were trained in a manner similar to that described in Example 1. To improve computation efficiency, a primal Newton method (as described in Chapelle, "Efficient algorithms for ranking with SVMs," *Inform. Retrieval* 13(3):201-215 (2010)) was employed to construct ranking models and generate predictions with a 10-fold cross-validation procedure. For each fold in the CV, speech improvement scores in the training set were converted into an ordered array and fed into the linear RankSVM to build models for each template. The predictive power of the resulting model was tested by calculating the Spearman's rank correlation between the predicted and observed speech improvement scores for the testing set ($\rho_{pred,obs}$). As in Example 1, a null distribution was also generated using 10,000 instances of randomly ordering the ranking scores of the data samples.

Figure 7A:
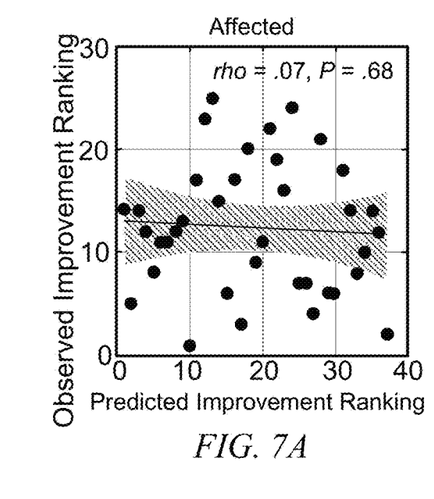
FIGS. 7A-7C show graphs of observed versus predicted improvement rankings for ranking SVM (RankSVM) models built according to various embodiments of the present invention from gray-matter MVPS using affected, unaffected, and whole-brain templates.
Figure 7B:
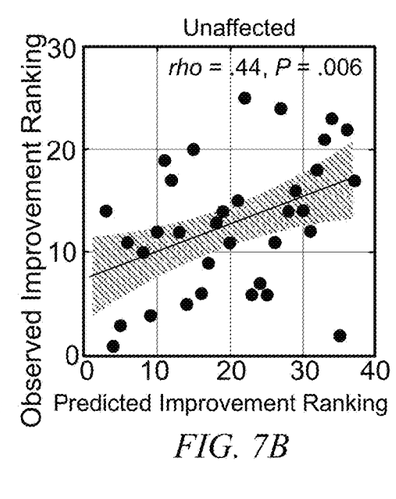
Figure 7C:
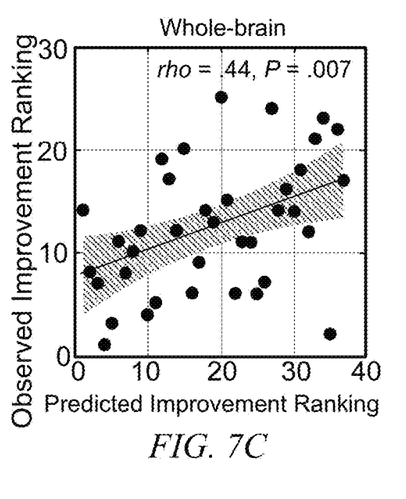
Figure 7D:
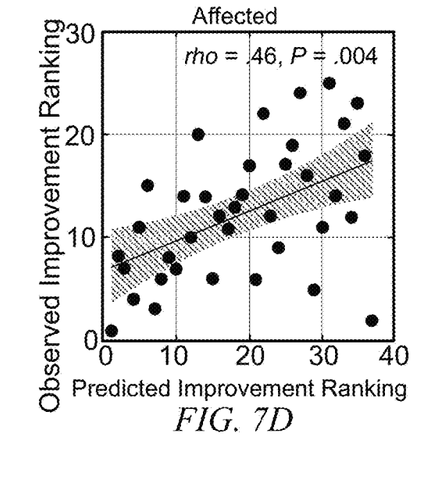
FIGS. 7D-7F show graphs of observed versus predicted improvement rankings for ranking SVM (RankSVM) models built according to various embodiments of the present invention from white-matter MVPS using affected, unaffected, and whole-brain templates.
Figure 7E:
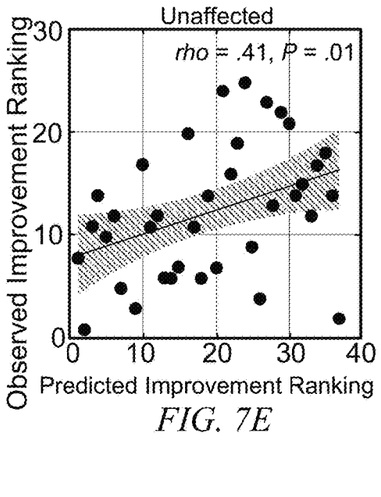
Figure 7F:
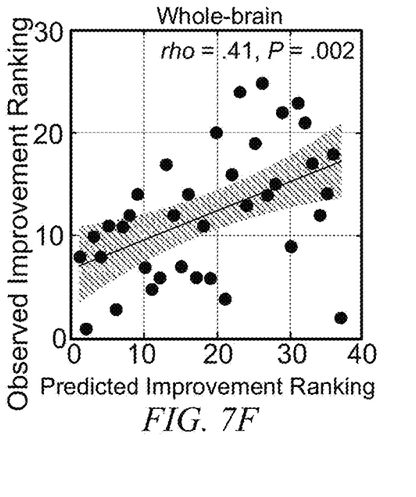

FIGS. 7A-7C show graphs of observed versus predicted improvement rankings for models built on GM and MVPS using affected, unaffected, and whole-brain templates, and FIGS. 7D-7F show graphs of observed versus predicted improvement rankings for models built on WM and MVPS using affected, unaffected, and whole-brain templates. Correlation values ($\rho_{pred,obs}$) are indicated.

Figure 7G:
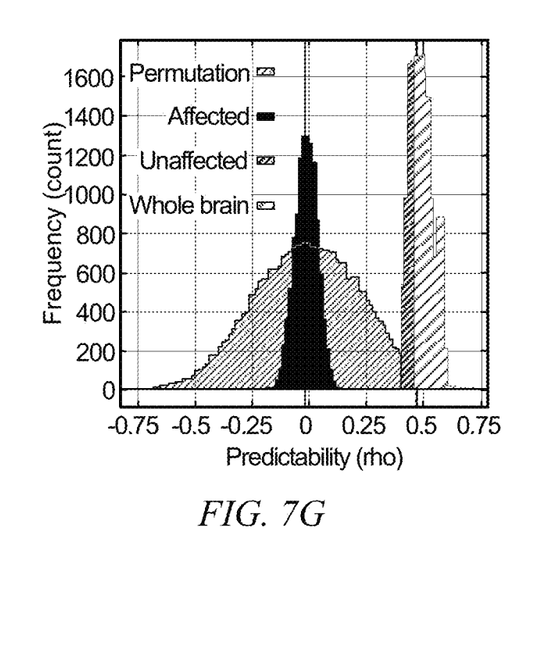
FIGS. 7G and 7H show histograms of the distribution of predictive power derived from RankSVM models built according to various embodiments of the present invention from gray-matter and white-matter MVPS using affected, unaffected, and whole-brain templates.
Figure 7H:
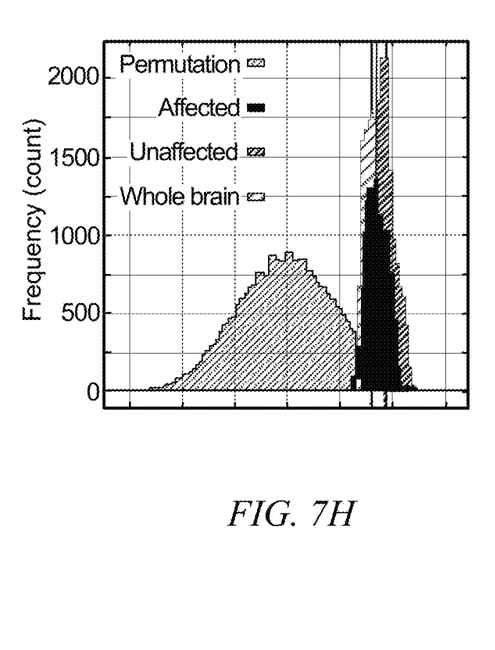

FIGS. 7G and 7H show histograms of the distribution of predictability ($\rho_{pred,obs}$) measured for different instances of the training procedure, for GM and WM MVPS respectively. Red bars correspond to training using a brain template that selected areas affected by auditory deprivation; green bars to a brain template that selected areas unaffected by auditory deprivation; blue bars to a whole-brain template. Gray bars show the null distribution.

As can be seen, the models performed significantly better than chance, except for models using the affected template in the GM MVPS measure.

Example 3: Whole Brain Searchlight Analysis

As another approach to analysis of brain-imaging data, a whole-brain searchlight classification analysis was also performed using the same data set described above. A searchlight algorithm is described in Kriegeskorte et al., "Information-based functional brain mapping," *Proc. Natl. Acad. Sci. USA* 103(10):3863-3868 (2006). A 10-fold cross-validation procedure was employed. At each voxel, local neuromorphological values (VBM density or MVPS) within a spherical searchlight (4-voxel-radius sphere) were extracted for each child. For each spherical searchlight, a V×C matrix was constructed, where V is the number of voxels in the searchlight and C is the number of children. This matrix was input to a linear SVM classifier for training and testing using LOOCV. Based on the results for different searchlights, a whole-brain classification accuracy map was generated. The classification map was thresholded using a null distribution generated by randomly assigning the children to low-improvement or high-improvement outcome groups and repeating the procedure 1000 times for each searchlight. Statistical significance was determined by comparing the actual classification accuracy and the permutation-based null distribution for each spherical searchlight.

Figure 8A:
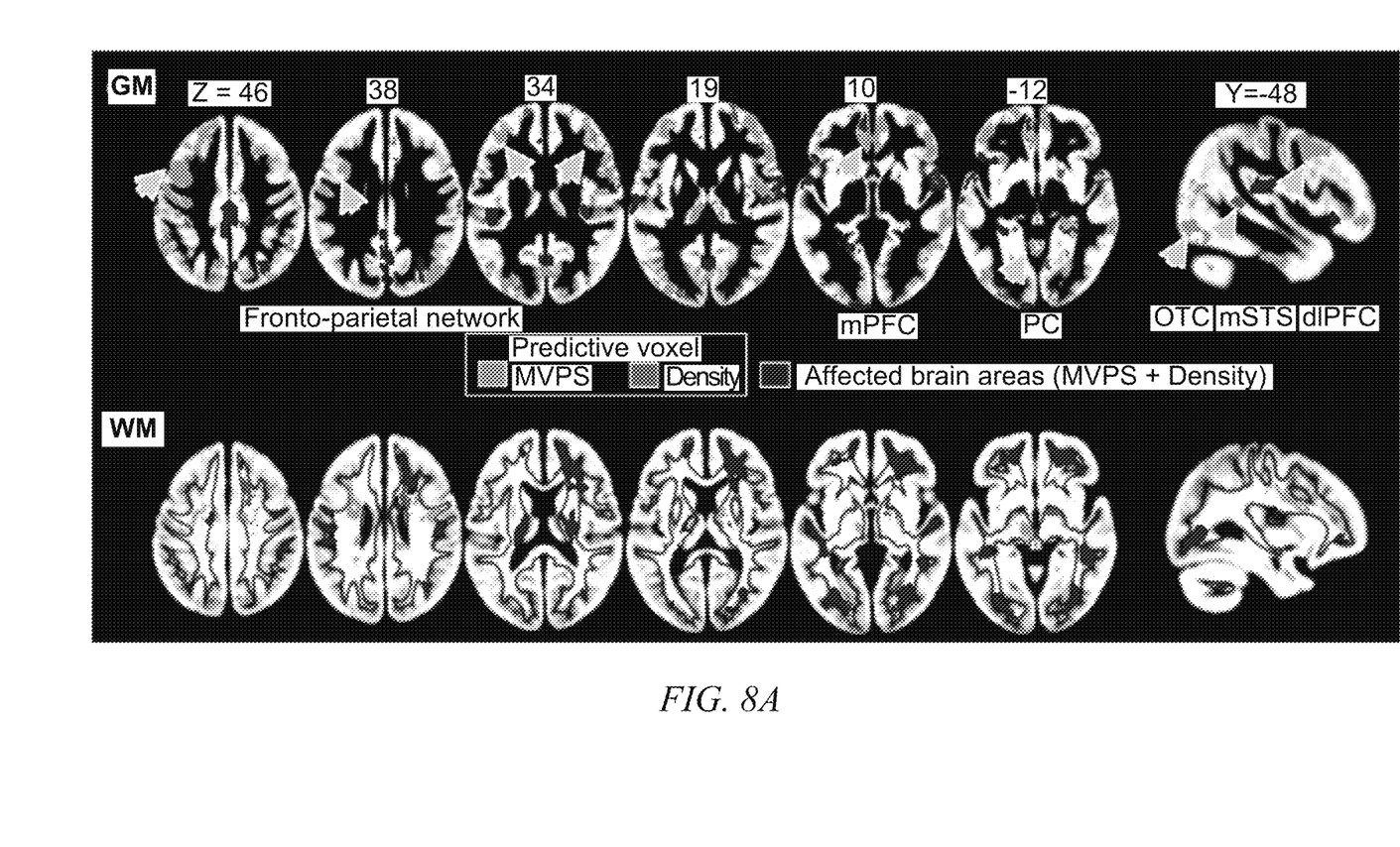
FIG. 8A shows brain maps highlighting regions identified in a searchlight analysis as best predicting the classification for MVPS (green) and VBM density (red) for gray matter (top row) and white matter (bottom row).

FIG. 8A shows brain maps highlighting the searchlight regions that best predicted the classification for MVPS (green) and VBM density (red), for GM (top row) and WM (bottom row). Blue areas indicate regions identified as affected by auditory deprivation. Yellow arrows point to the regions that showed the greatest classification accuracy. Brain regions shown include the fronto-parietal network, medial prefrontal cortex (mPFC), posterior cortex (PC), occipital-temporal cortex (OTC), middle superior temporal sulcus (mSTS), and dorsal lateral prefrontal cortex (dlPFC). As shown, the predictive regions are widely distributed across frontal, temporal, and parietal cortexes and include the left STG, which is known to be important for speech perception and learning, as well as numerous areas in the putative cognitive network such as the fronto-parietal cortexes.

Figure 8B:
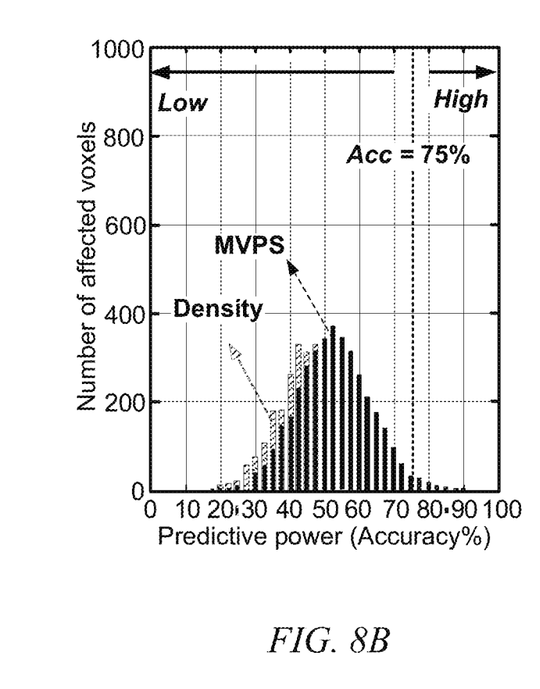
FIGS. 8B and 8C show histograms of the number of affected voxels having a given accuracy according to a searchlight analysis for MVPS and voxel-based morphometry (VBM) density, for gray matter (FIG. 8B) and white matter (FIG. 8C).
Figure 8C:
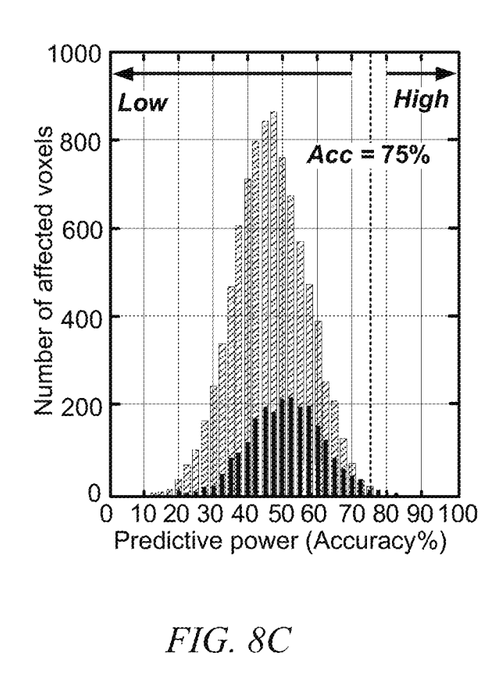
Figure 8D:
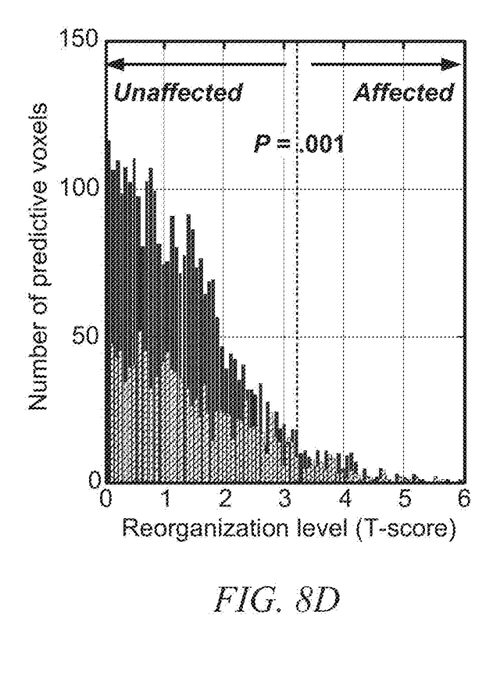
FIGS. 8D and 8E show histograms of the number voxels with high predictive power (significantly better than chance) as a function of reorganization level (t-score derived from a comparison of NH and CI children as described above), as determined from a searchlight analysis for gray matter (FIG. 8D) and white matter (FIG. 8E).
Figure 8E:
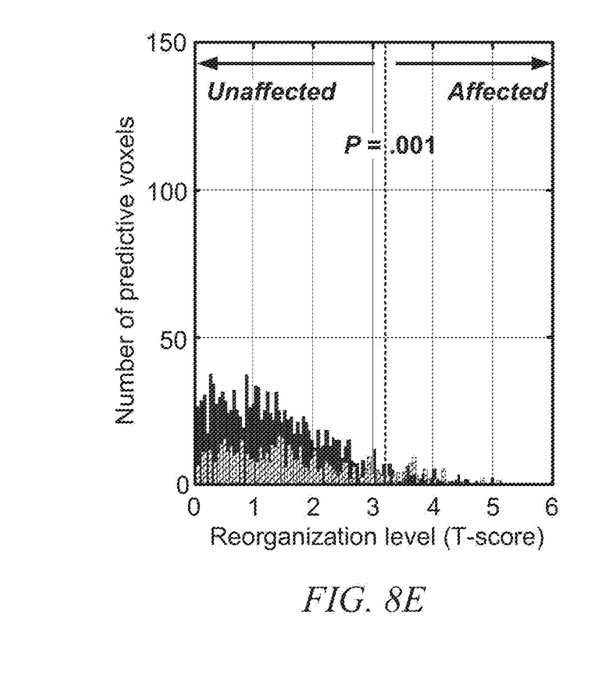

FIGS. 8B and 8C show histograms of the number of affected voxels having a given accuracy for MVPS (red bars) and VBM density (gray bars), for GM (FIG. 8B) and WM (FIG. 8C). Most of the affected voxels had low predictive power (accuracy less than 75%) in both cases. FIGS. 8D and 8E show histograms of the number voxels with high predictive power (significantly better than chance) as a function of reorganization level (t-score derived from a comparison of NH and CI children as described above), for GM (FIG. 8D) and WM (FIG. 8E). Lower t-score corresponds to voxels less affected by auditory deprivation. This analysis reinforces that voxels in brain areas affected by auditory deprivation have relatively low predictive effect while most voxels with high predictive effect are in unaffected brain areas outside of the primary auditory cortex.

Computer Implementation

Data analysis and computational operations of the kind described herein can be implemented in computer systems that may be of generally conventional design. Such systems may include one or more processors to execute program code (e.g., general-purpose microprocessors usable as a central processing unit (CPU) and/or special-purpose processors such as graphics processors (GPUS) that may provide enhanced parallel-processing capability); memory and other storage devices to store program code and data; user input devices (e.g., keyboards, pointing devices such as a mouse or touchpad, microphones); user output devices (e.g., display devices, speakers, printers); combined input/output devices (e.g., touchscreen displays); signal input/output ports; network communication interfaces (e.g., wired network interfaces such as Ethernet interfaces and/or wireless network communication interfaces such as Wi-Fi); and so on. Building and testing of classifiers as described herein (including linear SVM, nonlinear SVM, and RankSVM classifiers) can be supported using existing application software such as MATLAB or custom-built application software. Such software may be said to configure the processor to perform various operations, including operations described herein.

Computer programs incorporating various features of the present invention may be encoded and stored on various computer readable storage media; suitable media include magnetic disk or tape, optical storage media such as compact disk (CD) or DVD (digital versatile disk), flash memory, and other non-transitory media. (It is understood that "storage" of data is distinct from propagation of data using transitory media such as carrier waves.) Computer readable media encoded with the program code may be packaged with a compatible computer system or other electronic device, or the program code may be provided separately from electronic devices (e.g., via Internet download or as a separately packaged computer-readable storage medium).

In alternative embodiments, a purpose-built processor may be used to perform some or all of the operations described herein. Such processors may be optimized, e.g., for performing computations to train an SVM classifier, and may be incorporated into computer systems of otherwise conventional design or other computer systems.

Additional Embodiments

As described above, embodiments of the invention provide machine-learning techniques that can be used to train an automated classifier (e.g., SVM or RankSVM) to predict the degree of auditory and/or language skills improvement relative to a pre-CI baseline for an individual CI patient, based on imaging data representing structure of portions of the patient's brain. Depending on the particular classifier, the prediction can be binary (e.g., high improvement or low improvement) or quantitative (e.g., rank-based). The prediction can be used to inform treatment decisions and planning, although it is expected that treatment decisions will also consider other factors as well.

While the invention has been described with reference to specific embodiments and examples, those skilled in the art with access to the present disclosure will recognize that variations and modifications are possible. For instance, examples described above were based on data from patients who received CI prior to age 3.5 years. However, it is expected that similar processes could also be applied to other groups of patients, e.g., children up to age 8 years, older children, certain populations of adults, patients with unilateral hearing loss, and other groups as desired.

Brain-imaging data may be collected using a number of techniques, including but not limited to MRI. (MRI neuroimaging is already in use to evaluate candidates for CI, which means that the analysis described herein can be performed without requiring additional imaging of the patient.) As noted above, the MRI images used for the analysis described herein are anatomical rather than functional, and scans may be (but need not be) performed with the patient under sedation or general anesthesia, awake, or in natural sleep. Other imaging techniques may be used to produce neurological data characterizing brain composition in specific locations, including characterizations based on local tissue density (e.g., VBM), similarity in local spatial morphological patterns (e.g., MVPS) for gray matter and/or white matter, and functional and/or neurophysiological profiles (e.g., neural hemodynamic responses collected using functional MRI (fMRI) or optical imaging, electrophysiological responses measured by EEG or MEG, and so on). In some instances, including examples described above, imaging may be performed while the patient is not receiving any auditory stimulation. In some embodiments, the data used is structural/anatomical rather than functional, which may simplify the imaging process.

Brain templates for selecting brain areas (e.g., voxels or regions of interest) to analyze may be modified. As noted above, it appears that brain areas unaffected by auditory deprivation are more useful than brain areas affected by auditory deprivation, in terms of predicting improvement in speech processing skills; however, the invention is not limited to any particular selection of brain areas.

Classification of patients according to degree of improvement can be based on any measurement of language ability, including but not limited to the SRI-Q assessment battery or other tests described above. For a given patient, a baseline (pre-CI) assessment can be used as a reference point for the predicted improvement, allowing an overall assessment of likely outcome in terms of post-CI auditory and/or language skills.

A variety of classifiers (machine-learned algorithms that can be trained to predict an outcome for an unseen data sample based on a set of data samples with known outcomes) can be used. In examples described above, a linear or non-linear SVM provides an effective binary classifier that can be used to indicate whether the patient is likely to experience high or low improvement in auditory and/or language skills after CI. A RankSVM may allow a more quantitative prediction of the level of improvement, e.g., where outcomes are measured on an ordinal (non-continuous) scale, as is the case for SRI-Q. In embodiments where outcomes are measured on a continuous scale, other classifiers such as Support Vector Regression (SVR) may be used to provide quantitative predictions of the degree of improvement. Still other algorithms, such as Hidden Markov Model, and deep learning algorithms (e.g., artificial neural networks) may be substituted. The parameters used for training and testing the classifier may be varied, including the size of training data sets and number of voxels. A particular algorithmic implementation of training is not required.

Predicted outcomes generated in the manner described herein may be used in treatment planning. For example, the predicted outcome may inform the decision whether to proceed with CI for a given patient and/or decisions about appropriate post-surgical interventions (e.g., language-skills therapy, music and hearing therapy) in an individual case.

Thus, although the invention has been described with respect to specific embodiments, it will be appreciated that the invention is intended to cover all modifications and equivalents within the scope of the following claims.

What is claimed is:

1. A method of predicting an outcome of a cochlear implantation (CI) for a patient, the method comprising:

determining a baseline auditory and language skill level of the patient;

obtaining an image of at least a portion of the patient's brain;

extracting quantitative data from the image, the quantitative data including data characterizing at least one brain area that is associated with auditory and/or cognitive processing;

determining a predicted degree of improvement for the patient by analyzing the quantitative data using a machine-learning classifier that has been trained to predict a degree of improvement in language skill for an individual, wherein the training of the machine-learning classifier is based on corresponding quantitative data from a training data set obtained from a plurality of previous CI patients having known outcomes; and generating a predicted outcome of the CI for the patient based on the baseline auditory and language skill level and the predicted degree of improvement for the patient.

2. The method of claim 1 wherein the quantitative data includes data characterizing at least one brain area that is associated with auditory and/or cognitive processing and that is unaffected by auditory deprivation.

3. The method of claim 1 wherein the at least one brain area includes the ventral and/or dorsal auditory network.

4. The method of claim 1 wherein the at least one brain area includes one or more of the superior temporal region (STR) or the fronto-parietal cortices, or the occipital cortex.

5. The method of claim 1 wherein the image includes an image obtained by magnetic resonance imaging (MM).

6. The method of claim 5 wherein the MM is performed while the patient is sedated or under general anesthesia.

7. The method of claim 5 wherein the MM is performed while the patient is in natural sleep.

8. The method of claim 1 wherein the image includes an image of neuroanatomy.

9. The method of claim 1 wherein the image is obtained while the patient is not receiving auditory stimulation.

10. The method of claim 1 wherein the patient is under 8 years of age and wherein all of the previous CI patients were under 8 years of age when the training data was obtained.

11. The method of claim 1 wherein the patient is 3.5 years of age or younger and wherein all of the previous CI patients were 3.5 years of age or younger when the training data was obtained.

12. The method of claim 1 wherein the baseline auditory and language skill level is determined based on a direct response from the patient or an observer's appraisal of the patient's response.

13. The method of claim 1 wherein the predicted outcome includes a probable level of the patient's auditory and language skills after CI surgery.

14. The method of claim 1 wherein the machine-learning classifier is a support vector machine (SVM) and the predicted degree of improvement for the patient is either a high degree or a low degree.

15. The method of claim 14 wherein the SVM is a nonlinear SVM.

16. The method of claim 1 wherein the machine-learning classifier is a ranking support vector machine (RankSVM) and the predicted degree of improvement for the patient is quantified.

17. The method of claim 1 wherein the machine-learning classifier is a support vector regression algorithm (SVR) and the predicted degree of improvement is quantified.

18. The method of claim 1 wherein extracting the quantitative data from the image includes applying a template that selects at least one brain area that is not affected by auditory deprivation and excludes at least one brain area that is affected by auditory deprivation.

19. A computer system comprising:
a memory; and
a processor coupled to the memory and configured to:
  determine a baseline auditory and language skill level of a patient;
  obtain an image of at least a portion of the patient's brain;
  extract quantitative data from the image, the quantitative data including data characterizing at least one brain area that is associated with auditory and/or cognitive processing;
  determine a predicted degree of improvement for the patient by analyzing the quantitative data using a machine-learning classifier that has been trained to predict a degree of improvement in language skill for an individual, wherein the training of the machine-learning classifier is based on corresponding quantitative data from a training data set obtained from a plurality of previous CI patients having known outcomes; and
  generate a predicted outcome of the CI for the patient based on the baseline auditory and language skill level and the predicted degree of improvement for the patient.

20. The computer system of claim 19 wherein the quantitative data includes data characterizing at least one brain area that is associated with auditory and/or cognitive processing and that is unaffected by auditory deprivation.

* * * * *